United States Patent [19]

Strowe et al.

[11] Patent Number: 4,838,857
[45] Date of Patent: Jun. 13, 1989

[54] MEDICAL INFUSION DEVICE

[75] Inventors: Robert J. Strowe, Ramsey, N.J.; Floyd V. Edwards, Cedarville, Ohio; Carl M. Stern, Lawrenceville, N.J.

[73] Assignee: Becton, Dickinson and Company, Franklin Lakes, N.J.

[21] Appl. No.: 13,182

[22] Filed: Feb. 9, 1987

Related U.S. Application Data

[63] Continuation of Ser. No. 738,932, May 29, 1985, abandoned.

[51] Int. Cl.$^4$ ............................................. A61M 5/20
[52] U.S. Cl. ........................................ 604/67; 604/51; 604/65; 128/DIG. 12
[58] Field of Search ............... 128/DIG. 12, DIG. 13, 128/DIG. 1; 604/51, 52, 56, 65, 67, 118, 121, 131, 154, 155

[56] References Cited

U.S. PATENT DOCUMENTS

| | | | |
|---|---|---|---|
| 2,761,445 | 9/1956 | Cherkin | 604/121 |
| 3,425,416 | 2/1969 | Loughry | 604/155 |
| 3,701,345 | 10/1972 | Heilman et al. | 604/67 |
| 4,137,915 | 2/1979 | Kamen | 604/65 |
| 4,191,187 | 3/1980 | Wright | 604/155 |
| 4,210,138 | 7/1980 | Jess et al. | 604/123 |
| 4,278,085 | 7/1981 | Shim | 604/51 |
| 4,424,720 | 1/1984 | Bucchianeri | 604/155 |
| 4,457,750 | 7/1984 | Hill | 604/65 |
| 4,465,473 | 8/1984 | Rüegg | 604/154 |
| 4,465,474 | 8/1984 | Mardorf et al. | 604/154 |
| 4,468,219 | 8/1984 | George et al. | 604/67 |
| 4,475,901 | 10/1984 | Kraegen et al. | 604/67 |
| 4,498,843 | 2/1985 | Schneider et al. | 604/67 |
| 4,529,401 | 7/1985 | Leslie et al. | 604/67 |
| 4,544,369 | 10/1985 | Skakoon et al. | 604/155 |

FOREIGN PATENT DOCUMENTS 2451197 11/1980 France ................................ 604/155

Primary Examiner—Lee S. Cohen
Assistant Examiner—David Shay
Attorney, Agent, or Firm—Richard J. Rodrick; Aaron Passman

[57] ABSTRACT

A medication infusion device comprises a retainer for holding a medication-containing receptacle of the type which is actuatable to expel the contents of medication therefrom. A sensor is included for sensing a characteristic related to the amount of medication within the receptacle. A timing device allows the selection of the period of time over which the contents of the receptacle are to be expelled. A control mechanism, associated with the sensor and the timing device, actuates the receptacle to expel its contents at a controlled rate over the selected period of time.

36 Claims, 4 Drawing Sheets

MEDICAL INFUSION DEVICE

This application is a continuation of application Ser. No. 738,932, filed May 29, 1985, now abandoned.

BACKGROUND OF THE INVENTION

1. Field of the Invention

The present invention relates to a medication infusion deice, and more particularly, concerns a syringe infusion pump intended for the intravenous administration of medications.

2. Description of the Prior Art

Hospitals typically use intravenous (IV) administration sets to deliver liquids to patients. When the patient needs a drug, such as an antibiotic, it has been standard practice, until recently, to deliver such a drug by a "piggy-back" drip into the primary infusion line. Within the last several years, however, the procedure for delivering many drugs to patients on IV therapy has been changing. Mechanically driven syringes, also known as syringe infusion pumps, are now being used to handle the administration of drugs and similar medications.

Presently available syringe pumps for IV use are designed to operate at a constant speed or at a number of manually set, constant speeds. Once the syringe is positioned on the syringe pump, the syringe drive mechanism engages the plunger of the syringe and pushes the plunger at a constant speed into the syringe barrel so that the liquid contents are delivered to the patient over a fixed period of time. The time in which the medication is delivered to the patient is a function of the volume of fluid in the syringe. In order to meet the wide variation in syringe barrel dimensions for the different size syringes used in hospitals, it is presently necessary to have several different syringe pumps. Irrespective of the different syringe pumps for different size syringes, the syringe pumps remain constant speed devices.

When a drug is to be delivered to a hospital patient, the physician typically prescribes that a certain amount of the drug, by weight, be delivered to the patient over a period of time, usually in minutes. The hospital pharmacist usually must dilute the prescribed drug so that it may be delivered by use of a syringe pump. For presently available syringe pumps, however, which operate at constant speed, the pharmacist must calculate the volume of the diluted drug in order to be able to deliver that drug over the prescribed period of time. In many circumstances, the drug dilution calculated and prepared by the pharmacist is not the same drug dilution recommended by the drug manufacturer. As a result, drug dilutions, different from the recommended amount, may cause difficulties for fluid restricted patients or added complications occasioned by excessive drug concentrations. Accordingly, there is a present need to provide a syringe infusion device, for IV purposes, which may accommodate different size syringes and operate at different speeds so that drugs and medications may be delivered more conveniently and straightforwardly to the patient.

SUMMARY OF THE INVENTION

The medication infusion device of the present invention comprises means for holding a medication-containing receptacle of the type which is actuatable to expel the contents of medication therefrom. Means are provided for sensing a characteristic representative of the contents of medication within the receptacle. Means allow the establishment of the period of time over which the contents of the receptacle are to be expelled. Control means, associated with the sensing means and the time establishing means, allows the actuation of the receptacle to expel its contents at a controlled rate governed by the established period of time.

In a preferred embodiment of the present invention, a syringe infusion device is provided for the administration of liquid medication from a syringe having a barrel for holding medication and a plunger for expelling medication. The syringe infusion device of the present invention comprises a housing and a syringe retainer mounted on the housing. The retainer is adapted to hold the syringe and to receive different size syringe barrels therein. A movable syringe driver is mounted on the housing and is adapted to engage the syringe plunger and push the plunger into the syringe barrel to thereby force the liquid contents out of the syringe barrel. Sensor means are included for determining the distance the syringe plunger must travel to expel the contents of the barrel. The sensor means also provide information related to the determined distance. Control means move the syringe driver against the plunger to expel the contents of the syringe barrel over a pre-selectable period of time at a rate of speed governed by information received from the sensor means relating to the distance determination. A visual display monitors the period of time over which the contents of the syringe barrel are expelled.

In accordance with the principles of the present invention, many of the aforementioned problems and deficiencies associated with presently available syringe pumps are overcome. Most notably, the present invention permits the administration of a drug or the like as a direct implementation of the physician's prescription. Further, the present invention permits the utilization of any size syringe, but preferably those syringes ranging from 3 cc to 60 cc. Furthermore, the medication infusion device of the present invention may be set, by the user, to deliver the medication over a variable period of time, which is preferably from 10 to 60 minutes. As a result of the features of the present invention, the hospital pharmacist may mix the prescribed drug directly to the manufacturer's recommended dilution, and may use any appropriate size syringe to hold the resulting liquid volume. To complete the administration of the prescription drug to the patient, the hospital attendant merely selects the prescribed time for the drug delivery, or relies on the time automatically set by the device, when the infusion procedure is ready to begin.

There are a number of features of the present invention which facilitate the advantages as noted above. Because there are large variations in the height of the plunger of an empty syringe, there is a sensor incorporated into the syringe retainer of the present invention. This sensor makes a determination which specific size syringe is mounted in the syringe infusion device. Preferably, this sensor makes a determination which one of 3,5,10,20,30 or 60 cc syringes is in the syringe pump. Also, since there are variations in the height of the plunger in the filled syringe, there is another sensor which determines this height with reference to the finger flanges at the proximal end of the syringe. In addition, and in order to provide better prescription control, the present medication infusion device is equipped with a special display. This display allows the attending medical team to monitor not only the time remaining for infusion, but also the original infusion time setting. Other advantages and features of the present invention will be perceived upon a reading of the detailed description which follows.

DETAILED DESCRIPTION

Figure 1:
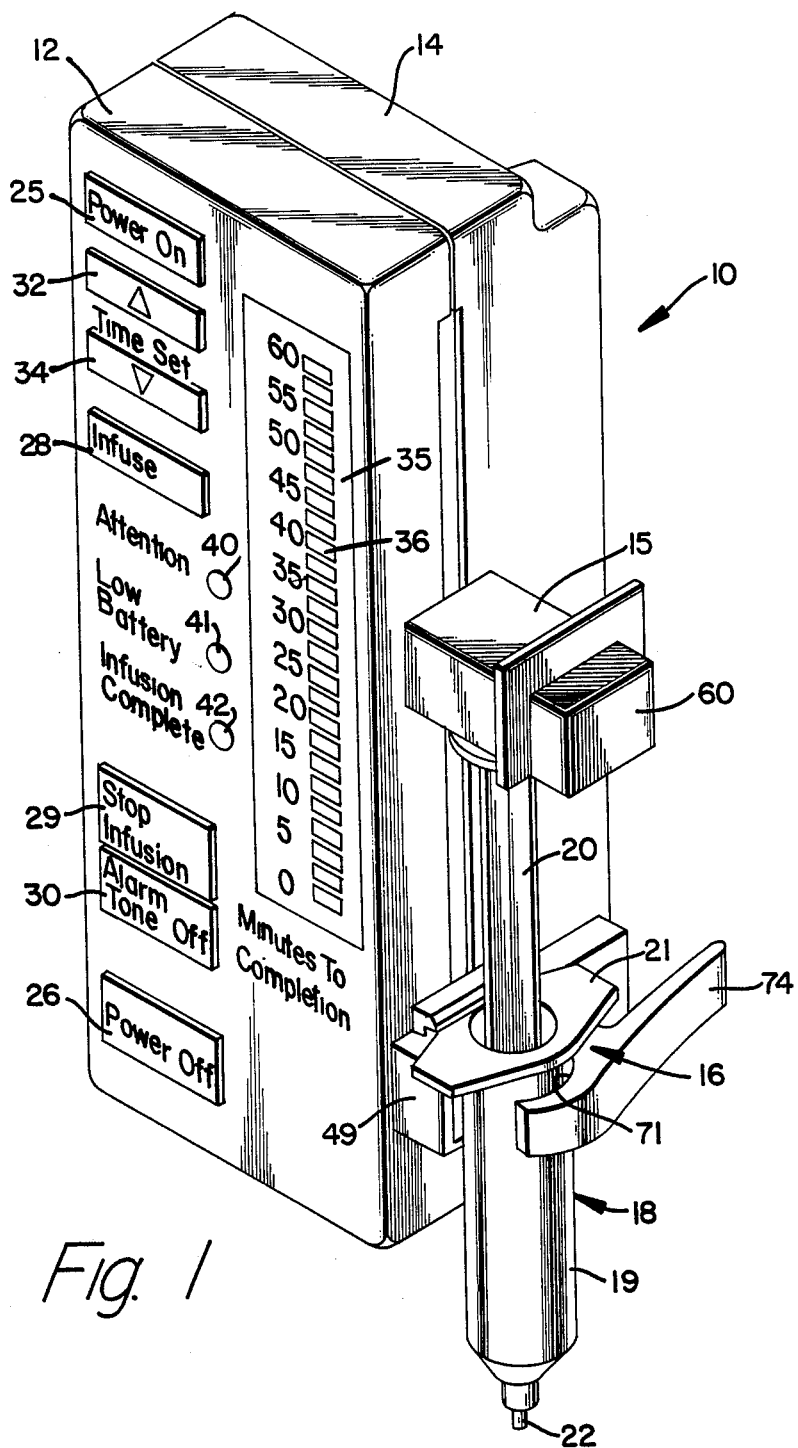
FIG. 1 is a perspective view of the preferred configuration of a syringe infusion device of the present invention illustrated with a syringe loaded in position.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting now to the drawings, and FIG. 1 in particular, there is illustrated the preferred medication infusion device of the present invention in the form of a syringe infusion pump 10. The primary, externally visible components of infusion pump 10 include a top or cover section 12, a bottom or back section 14, a driver mechanism 15 and a syringe retainer device 16. As seen in FIG. 1, a medication-containing receptacle, preferably in the form of a syringe 18, is mounted in the infusion pump as it would appear prior to its use for delivering drugs or medications, particularly during IV therapy. It can be seen that syringe 18 includes two main components, a syringe barrel 19 and a plunger 20. A finger flange 21 facilitates the mounting of the syringe into retainer 16 of the infusion pump. At the distal end of the syringe barrel is an opening 22 through which liquid contents of the syringe barrel are expelled when plunger 20 moves inwardly into syringe barrel 19.

Top section 12 and bottom section 14 of the present infusion device form a housing into which the control mechanisms for operation of the device are incorporated. A number of user controls, indicators and displays associated with such control mechanisms, are included on the outside panel of top section 12. The user controls include a POWER ON button 25 and a POWER OFF button 26. An INFUSE button 28 is provided to start the operation of syringe driver 15, whereas the STOP INFUSION button 29 is included for terminating the operation of the infusion device. An ALARM TONE OFF button 30 permits the user to stop an audible alarm which activates in the event of a malfunction or other problem related to delivering the contents of the syringe. Two TIME SET buttons 32 and 34 are associated with a visual timing mechanism 35 displayed on the front panel of cover section 12. As will be described more fully hereinafter, TIME SET button 32 permits the user to incrementally increase the time of operation from the automatically pre-set time, whereas TIME SET button 34 allows the user to incrementally decrease the time of operation. An ATTENTION indicator light 40 is provided to visually inform the user that a malfunction or problem is occurring. A LOW BATTERY indicator light 41 indicates that the batteries are low on energy and should be changed. The final indicator light 42 is an INFUSION COMPLETE indicator to visually indicate when the movement of syringe plunger 20 by driver 15 has been completed.

Figure 2:
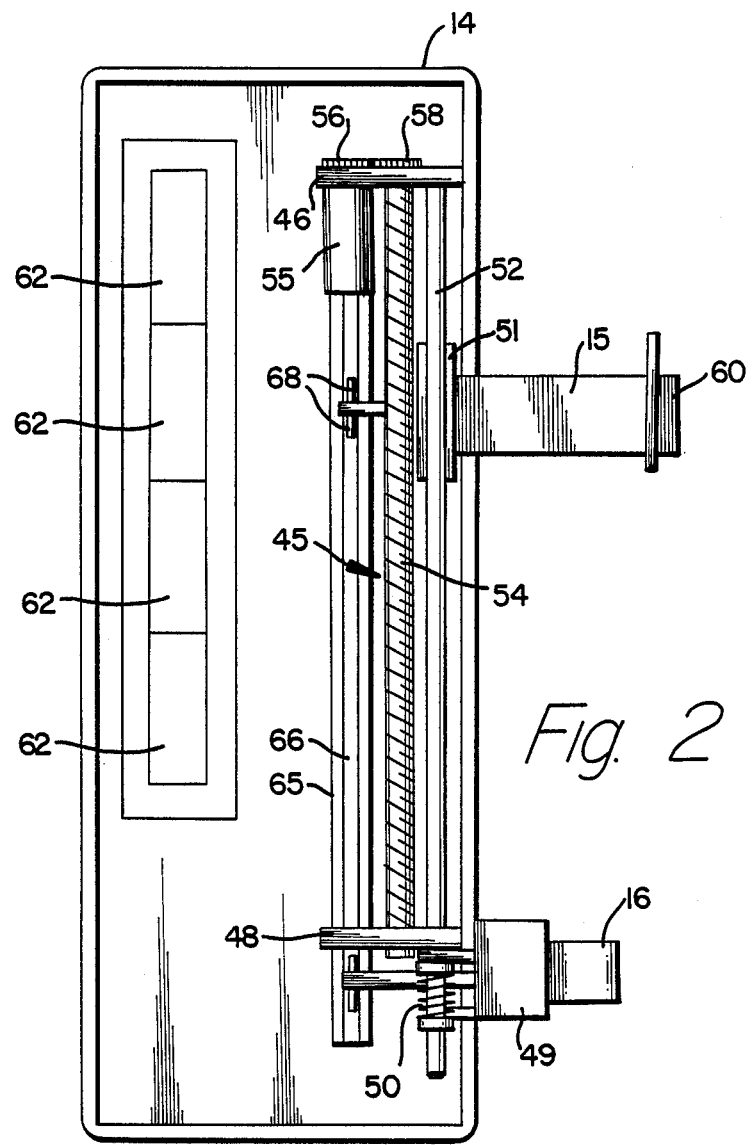
FIG. 2 is a plan view of the bottom section of the syringe infusion device of FIG. 1 illustrating the syringe driver and retainer assembly mounted in position.
Figure 3:
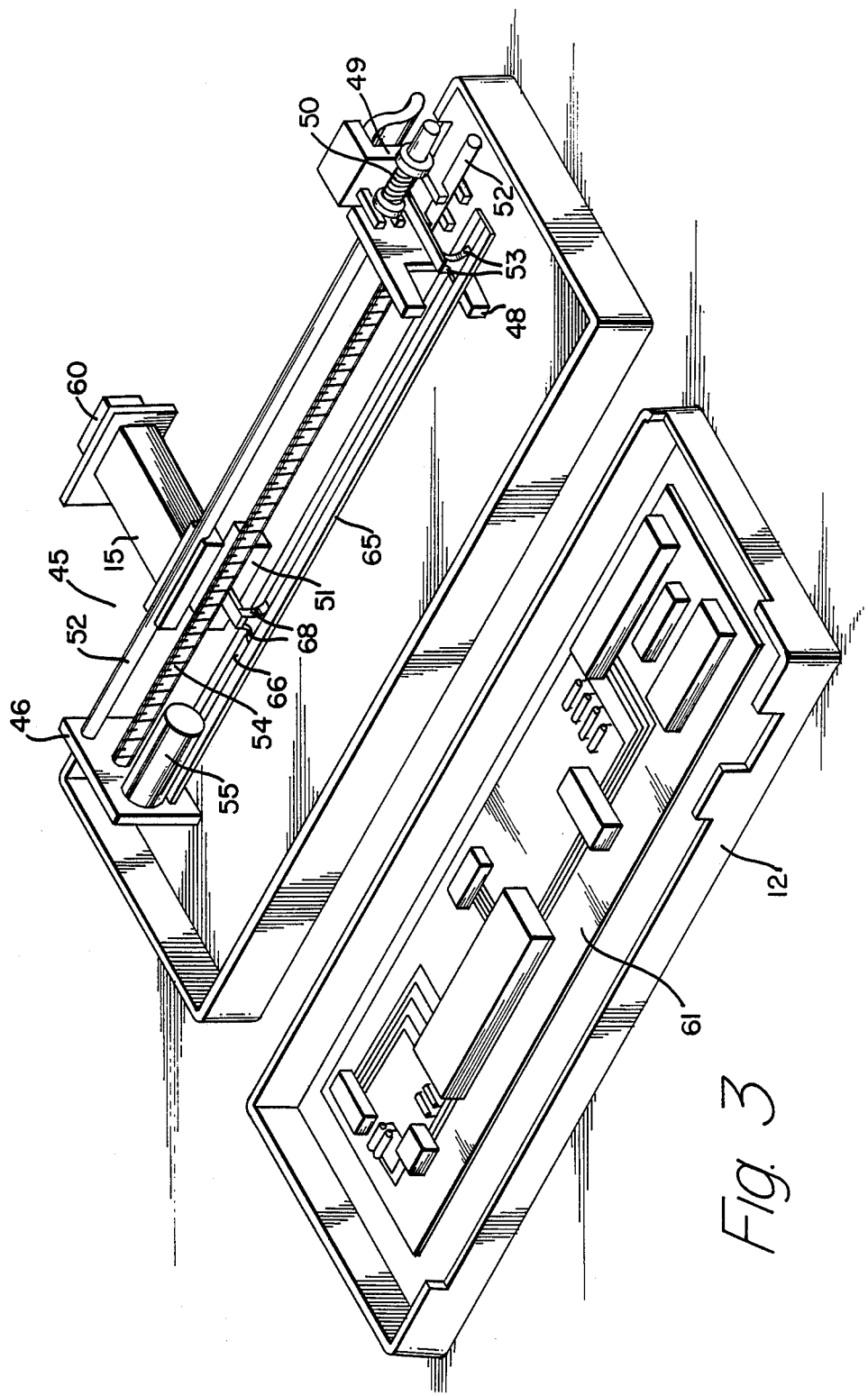
FIG. 3 is a perspective view of the syringe infusion device of FIG. 1 with the top section removed to reveal the interior details thereof.

Referring now to FIGS. 2 and 3 which illustrate the interior components of the present infusion device in more detail, driver assembly 45 is shown mounted in bottom section 14 of the infusion device. Syringe driver 15 and clamp 16 are oriented so that they protrude outwardly from the side of bottom section 14. Driver assembly 45 is mounted within bottom section 14 by virtue of a pair of mounting plates 46 and 48 on opposite sides of the driver assembly. Syringe retainer 16, preferably in the form of a clamp, is hingedly connected to a mounting block 49. Both clamp 16 and block 49 are retained within guide rails 52 and are free to move against spring 50. Attached to block 49 and contacting potentiometer strip 66 is electrical contactor 53. Components 16, 49, 66, and 53 form the mechanical elements of the occlusion detector, as will be described in more detail hereinafter.

On the other hand, driver 15 is intended to impart linear motion to syringe plunger 20. To that end, driver 15 is connected to a mounting block 51 which slides on one or more guide rails 52 extending between mounting plates 46 and 48. Mounting block 51 is also provided with a mechanism for mating with the threads of a jack screw 54, also extending between mounting plates 46 and 48. A variable speed motor 55 is mounted on plate 46, and has a drive shaft (not shown) extending through the mounting plate and connected to a rotatable gear 56. This gear meshes with another gear 58 connected to jack screw 54 so that the motor can turn the jack screw and therefore move driver 15 in a rectilinear direction substantially along the length of the jack screw.

Driver 15 is further equipped with a release button mechanism 60 which permits driver 15 to become temporarily disconnected from jack screw 54. In this regard, activation of release button 60 serves as a mechanism which normally maintains the driver in actuating engagement with jack screw 54. Mechanism 60 is manually releasable to disengage the driver from jack screw 54 so that driver 15 is freely movable on guide rail 52. This free movement permits the user to position the syringe in place and to accommodate the height of syringe plunger 20 against which driver 15 is intended to make engagement.

FIGS. 2 and 3 further illustrate the inclusion of the electrical components 61 which cooperate with driver assembly 45, as well as the panel-mounted controls, indicators and display, to render the present infusion device operable. It is expected that state of the art electrical components may be selected and utilized to achieve the features consistent with the description of the present invention. Operation of the present infusion device, however, is preferably regulated by a microprocessor included within the electrical components, in conjunction with a closed loop servomechanism for controlling the speed of motor 55 and thereby the linear speed that syringe driver 15 moves along jack screw 54. This microprocessor-based control mechanism for the present device is capable of being programmed to accept information with respect to size of the syringe barrel and height of the syringe plunger, as will be pointed out hereinafter. To render the present infusion device portable, electrical energy is preferably provided by one or more batteries 62, shown schematically in FIG. 2.

Turning more particularly to FIG. 3, it can be seen that driver assembly 45 includes a linear potentiometer 65 extending substantially parallel to jack screw 54 and extending substantially between mounting plates 46 and 48. This linear potentiometer includes an electrically conductive strip 66. Mounting block 51, associated with syringe driver 15, includes a pair of electrical contacts 68 which contact linear potentiometer 65 and cooperate with conductive strip 66 to develop a position-sensitive electrical resistance. Thus, an analog voltage may be developed which changes according to the position of syringe driver 15 with respect to syringe retainer clamp 16. The position-sensitive analog voltage is thus representative of the height that the plunger extends out of the syringe barrel when mounted on the infusion device. By sensing this analog voltage, the microprocessor knows the distance that syringe driver 15 must travel in order to bottom-out against syringe clamp 16. With syringe 18 properly mounted on the infusion device, the aforementioned distance of travel of driver 15 is analogous to the distance plunger 20 must travel within syringe barrel 19 to expel the liquid contents therefrom.

Figure 4:
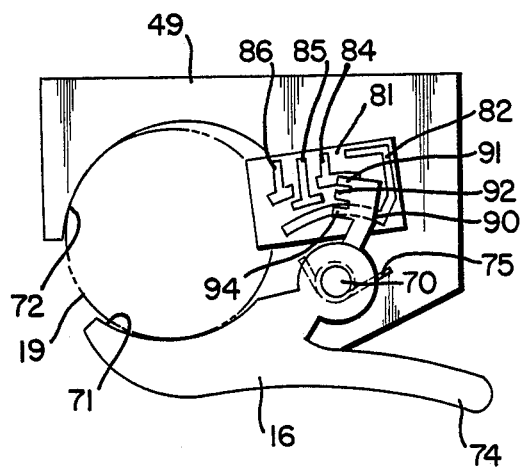
FIG. 4 is a top plan view of the preferred syringe retainer in the form of a clamp schematically illustrating the clamping and sensing of the syringe barrel.

FIG. 4 illustrates in greater detail the function of syringe clamp 16 so as to be able to receive and hold different size syringe barrels. Clamp 16 is pivotally mounted, by means of pivot pin 70, to mounting block 49. Clamp 16 is provided with an arcuate cut-out portion 71 and block 49 has a similar arcuate portion 72. These arcuate portions facilitate the receipt of the round diameter of syringe barrel 19 therebetween. Clamp 16 further includes a thumb lever 74 so that the user may push against this lever to manually move clamp 16 to an open position to insert the syringe barrel between the arcuate surfaces. A spring 75 is associated with pivot pin 70 so that arcuate surface 71 of the clamp is normally biased toward arcuate surface 72 of the mounting block. In this regard, different size syringe barrels may be positioned between the two arcuate surfaces of this grasping arrangement to thereby hold the syringe barrel in fixed position during the infusion procedure.

Affixed to mounting block 49 is an insulator board 80 with a plurality of electrically-conductive pads 82, 84, 85 and 86. The number of electrically-conductive pads as herein described is merely for exemplary purposes, and is not intended to limit the invention to any fixed number. Although not shown in FIG. 4, wires are connected to the respective electrical pads for connection to the electrical control means as hereinbefore described. Protruding from clamp 16 is an electrical insulator 90 from which extends a plurality of electrically conductive tabs 91, 92 and 94. These tabs are also preferably wire-connected (not shown) to the electrical controls of the present invention. It can be seen that the electrical tabs associated with the clamp are positioned to contact the electrical pads associated with the mounting block. The electrical tabs contact different pads depending upon the position of arcuate surface 71 with respect to arcuate surface 72. Thus, syringe barrel 19 (illustrated in phantom in FIG. 4) of one size causes certain pads to be contacted by the tabs, whereas a different size syringe barrel causes other pads to be contacted by the tabs. This syringe barrel diameter sensing arrangement is intended to make a gross diameter scan of the syringe barrel and categorize the barrel as belonging to a syringe of a certain size.

Most commonly used syringes for hospital purposes have designations based on total volume and have an outside diameter which is a function of the volume. In the present sensing arrangement described herein and illustrated in FIG. 4, and merely for exemplary purposes, six different size syringes may be sensed depending upon which electrical pads are contacted by the tabs. For instance, if a 10 cc syringe is positioned between arcuate surfaces 71 and 72, pads 82 and 85 may be contacted by the electrical tabs associated with the clamp. The microprocessor control elements may be programmed to acknowledge that, when pads 82 and 85 are in electrical contact, a 10 cc syringe is in place in the infusion device. In similar fashion, different standard size syringes may be sensed by the mechanism herein described. It is preferred that the present invention permit the sensing of at least 3,5,10,20,30 and 60 cc syringes. Once the microprocessor acknowledges the size of the syringe positioned in the infusion device, the sensed size information is used to govern the rate of movement of the syringe driver which actuates the syringe plunger.

Operation of the infusion device, and features of the device associated with its operation, will now be described. Syringe 18, preferably being one of the six sizes mentioned above, is typically prefilled by the pharmacist and contains a diluted quantity of a drug to be administered to the patient. Plunger 20 typically extends outwardly from syringe barrel 19 when the syringe barrel has liquid contents therein, as represented by the appearance of the syringe in FIG. 1. The syringe is positioned in the infusion device by a few simple manipulative steps. The user depresses release button 60 and lifts syringe driver 15 upwardly; thumb lever 74 of clamp 16 is then depressed so that syringe barrel 19 is positioned between arcuate surfaces 71 and 72. In positioning the syringe, it is preferred that flange 21 at the proximal end of the syringe barrel rest against the top of mounting block 49, as seen in FIG. 1. Then, the user once again depresses release button 60 of driver 15, and lowers the driver until it engages the upper end of plunger 20. No matter what the size of the syringe, its volumetric contents or the height that the plunger extends from the syringe barrel, the procedure for loading the syringe onto the infusion device is the same as described above. Prior to operation, an appropriate tubing connection is made between opening 22, at the distal end of the syringe barrel, and the patient.

To commence operation, POWER ON button 25 is depressed. With the microprocessor and electrical components turned on, the device is programmed to run through diagnostic procedures in which all of the alarm indicators are energized and time display 35 set for the operating mode. As seen in FIG. 1, time display 35 includes a series of lights, LED's or LCD segments 36 each representative of 2.5 minute increments. Thus, in the embodiment being described, the operating time range for a single procedure extends from 10 to 60 minutes. When the infusion device is turned on, the time setting of the timing mechanism of display 35 is automatically set at 30 minutes, which corresponds to the most common delivery time for administering medications to patients. This automatically set time is merely for convenience purposes, and may be pre-set to a different time, if desired. In the event that the delivery time is prescribed for a time other than 30 minutes, the user may make an alteration by depressing TIME SET button 32 to increase the delivery time or by depressing TIME SET button 34 or to decrease the delivery time. Such alteration is accomplished in 2.5 minute segments, and the LCD 36 corresponding to the selected time to complete the infusion remains lighted.

To initiate the infusion procedure, INFUSE button 28 is manually depressed. This activates the microprocessor and servo system, as described above, so that movement of syringe driver can be started. However, before syringe driver 15 is put into motion, the depression of the INFUSE button causes the microprocessor to scan syringe barrel 19 by virtue of the sensor mechanism incorporated within clamp 16, and as described in detail in conjunction with FIG. 4. The size of syringe barrel 19 is determined by the clamp sensor so that the microprocessor can relate that size with one of the pre-determined syringe sizes. Information about syringe size is used by the microprocessor to call up information with respect to the height of the plunger in an empty syringe of the same size. Plunger heights of empty syringes, i.e., the plunger all the way into the syringe barrel, of the six pre-selected sizes may be pre-fed into the memory of the microprocessor.

In conjunction with the sensing mechanism associated with linear potentiometer 65, the microprocessor receives position-sensitive information related to the height of the plunger rod of the filled syringe. The microprocessor is pre-programmed to subtract the pre-known height of the plunger of the empty syringe from the height of the plunger of the filled syringe. As a result, a determination is made for the distance that plunger 20 must travel in order to expel the contents of the syringe barrel. With the time of delivery previously entered and displayed on time display 35, the microprocessor calculates the appropriate motor speed of motor 55 (shown in FIG. 2) which controls the rate of speed of syringe driver 15. Linear motion of syringe driver 15 is imparted to plunger 20 to thereby push the plunger into the syringe barrel for expelling the liquid contents at a controlled rate. For purposes of the present invention, but without limiting the invention thereto, syringe driver 15 may travel within a speed range of 1 inch per hour (2.5 cm per hour) to 25 inches per hour (62.5 cm per hour). During the delivery of liquid medication, the microprocessor continually scans for the plunger position, in conjunction with the linear potentiometer, to determine its position and to alter the motor speed if necessary.

Should the plunger position relative to clamp block 49 not change, as might result in the case of a clogged infusion, the microprocessor is programmed to stop power to the motor and to energize the alarms, including the ATTENTION indicator 40. In addition, an audible alarm is sounded when ATTENTION indicator 40 is activated. In the alarm condition, movement of syringe driver 15 is stopped. The alarm condition of the present invention is preferably related to a maximum force which syringe driver 15 may deliver to plunger 20. This force is developed by the movement of clamp block 49 against spring 50. The movement of clamp block 49 is sensed by measuring the voltage change of wiper 53 as it moves down potentiometer strip 66. When that force reaches a threshold, the microprocessor considers such force level as an occlusion or clogged infusion, so that movement of the syringe clamp is terminated and the alarm is activated. For each of the different size syringes, a maximum force to be delivered by the driver is pre-programmed into the microprocessor thereby establishing thresholds for initiating the alarm condition. Thus, if a clogged infusion occurs while there is time remaining for delivery of the medication, movement of the syringe driver will be automatically stopped. The alarm condition is permitted to continue until the user depresses STOP INFUSION button 29. Once the impediment causing the alarm condition has been removed, infusion may continue by once again depressing INFUSE button 28.

When syringe driver 15 is operating to push plunger into syringe barrel 19 to expel the liquid contents, INFUSE button 28 is designed so that it blinks to indicate correct operation; at the same time, the LCD indicative of time remaining on time display 35 also flashes. The flashing time segment continues to move down display 35 to indicate the time to complete the infusion. Driver 15 continues to expel fluid until the plunger bottoms in the syringe. At this point, the unit would appear to have an occlusion as all further movement of the plunger moves the syringe clamp block 49. In order to allow for all tolerances present in syringe components, an occlusion sensed in the last 2.5 minutes of delivery is considered as a completed infusion. When the infusion has been completed, the blinking of the INFUSE button ceases, and the INFUSION COMPLETE indicator light 42 is energized. The LED of time display 35 corresponding to 0 time is lighted when the infusion has been completed. Furthermore, when infusion has been completed, movement of syringe driver 15 is automatically terminated since the contents of the syringe barrel have been expelled. Another feature of the present invention relates to the display of the original time which had been selected for the complete infusion procedure. Thus, when the flashing LED's move downwardly along display 35 to indicate the time remaining to complete the infusion, the LED corresponding to the originally pre-selected time continues to remain lighted throughout the complete infusion period.

It should also be pointed out that STOP INFUSION button 29 may be activated by the user at any time during the infusion procedure to terminate movement of syringe driver 15 against plunger 20, irrespective of whether an alarm condition exists. In the STOP INFUSION mode, the LED corresponding to the original pre-set time and the LED corresponding to time remaining for infusion continue to be displayed.

Thus, it can be seen that the medication infusion device of the present invention is not only portable but may be used with syringes or like receptacles of many different sizes. Syringe size is automatically assessed by the present device, as is the distance that the plunger must travel to expel the contents from the syringe. This syringe size and plunger distance information is utilized by the microprocessor-regulated servomechanism to control the speed of the motor, drive mechanism and syringe driver. Most advantageously, the medication infusion device of the present invention permits the hospital attendant to directly implement the physician's prescription. The pharmacist may mix the prescribed drug or medication directly in accordance with the manufacturer's recommended dilution, and use any appropriate size syringe to hold the resulting liquid volume. To deliver the prescription, the attendant simply loads the filled syringe into the infusion device, selects the prescribed time for delivery, and pushes a button whereupon infusion automatically occurs at the prescribed rate.

What is claimed is:

1. An infusion device for the administration of liquid from a syringe having a barrel for holding liquid and a plunger for expelling liquid comprising:
   a housing;
   a syringe retainer mounted on said housing for receiving therein a syringe barrel having liquid therein, said retainer including means for receiving syringe barrels of different sizes;
   a movable syringe driver mounted on said housing adapted to engage a syringe plunger and push the plunger from a relative initial position into the syringe barrel to a relative final position to thereby force the liquid out of the syringe barrel, said initial position of the plunger being relative according to the amount of liquid within the syringe barrel;
   sensor means for determining the size of the syringe barrel mounted on the housing, for determining said final position which is relative depending upon the size of the syringe barrel mounted on the housing, and for determining the relative distance the syringe plunger must travel from said initial position to said final position to expel the liquid from the barrel, and for providing information related to said determined distance;
   control means for moving said syringe driver against said plunger to expel the liquid from said syringe barrel over a pre-selectable period of time at a rate of speed governed by said information received from said sensor means relating to the distance determination; and
   a visual display for monitoring the period of time over which the liquid from said syringe barrel is expelled.

2. The device of claim 1 wherein said retainer includes a manually operative clamp of such size and shape to grasp different diameter syringe barrels.

3. The device of claim 2 wherein said clamp is spring-biased in order to facilitate maintaining the barrel in fixed position with respect to said housing.

4. The device of claim 1 wherein said sensor means includes a sensor associated with said driver for determining the initial position of said plunger with respect to said syringe barrel with liquid therein to relate said initial position to the distance said plunger must travel within said barrel to said final position to expel the liquid over the selected period of time.

5. The device of claim 4 wherein said driver sensor is a linear position sensor.

6. The device of claim 1 wherein said syringe driver is slidably mounted to said housing and associated with said control means to impart linear motion to the plunger when engaged therewith.

7. The device of claim 1 wherein said syringe driver includes a locking mechanism which normally maintains said driver in actuating engagement with said control means and which is manually releasable to disengage the driver from said control means to permit the driver to freely move so that the syringe barrel may be positioned in the retainer and the driver moved into position against the plunger.

8. The device of claim 1 wherein said sensor means includes a sensor associated with said retainer which scans an outside diameter of the syringe barrel positioned within the retainer.

9. The device of claim 8 wherein said retainer sensor includes means for providing information to said control means that the syringe barrel represents a syringe of one of a series of sizes pre-programmed into said control means.

10. The device of claim 1 wherein said control means includes a controllable motor and drive mechanism for moving the syringe driver.

11. The device of claim 10 wherein said control means further includes a microprocessor regulated servo system for controlling speed of said motor and drive mechanism.

12. The device of claim 11 wherein said control means further includes a variable timing device wherein the period of time, over which the liquid from said syringe barrel is to be expelled, is selectable by a user.

13. The device of claim 12 wherein said timing device includes automatic means for setting the timing device at a pre-determined time period, for expelling the liquid from said syringe barrel, when a syringe is positioned in said retainer.

14. The device of claim 13 wherein said control means includes a timing stepper to permit the user to incrementally select a time period for operation either longer of shorter than the automatically set, pre-determined time.

15. The device of claim 1 wherein said control means includes manually accessible switch means for initiating the movement of the syringe driver.

16. The device of claim 1 wherein the control means includes means for automatically stopping movement of the syringe driver when the period of time for operation has substantially expired.

17. The device of claim 16 wherein the means for automatically stopping movement of the syringe driver is further operable when the period of time has not expired and an event occurs indicative of an impediment to expelling the liquid from the syringe barrel.

18. The device of claim 16 which further includes an alarm which becomes activated if the period of time has not expired and the movement of the syringe driver stops.

19. The device of claim 1 wherein the control means includes manually accessible switch means for stopping the movement of the syringe driver at any time during the period of time of operation.

20. The device of claim 1 wherein said display is a timing mechanism which visually indicates the time remaining to expel the liquid from the syringe barrel.

21. The device of claim 20 wherein said display further includes an indicator which continually displays the original, selected period of time for expelling the liquid from the syringe barrel during the period when liquid is being expelled.

22. A medication infusion device comprising:
   means for holding a medication-containing receptacle of the type including linearly movable means for expelling the contents of medication therefrom;
   means for sensing a relative beginning point and a relative ending point defining a linear distance that the movable means must travel to expel the medication from the receptacle, said ending point being relative according to the size of the receptacle;
   means, associated with said sensing means, for establishing a period of time over which the contents of said receptacle are to be expelled; and
   control means associated with said characteristic sensing means and said time establishing means for actuating said receptacle to expel its contents at a controlled rate governed by said established period of time.

23. The device of claim 22 wherein said means for establishing includes timing means for automatically setting the time period for expelling the contents of the receptacle.

24. The device of claim 22 wherein said means for establishing includes timing means for permitting the user to select the time period for expelling contents of the receptacle.

25. The device of claim 22 wherein said means for holding is variable to accept receptacles of different cross-sectional areas and wherein said sensing means includes means for sensing at least one dimension which is a function of cross-sectional area of said receptacle.

26. The device of claim 22 which further includes display means for monitoring the period of time over which the contents of said receptacle are to be expelled.

27. An infusion device for the administration of liquid from a syringe having a barrel for holding liquid and a plunger for expelling liquid from said barrel comprising:
a housing;
a manually operative clamp mounted on said housing for holding a syringe barrel and having such size and shape to grasp syringe barrels having different outside diameters;
a first sensor mounted on said clamp for scanning the outside diameter of the syringe barrel positioned within the clamp to determine the size of the barrel mounted on the housing and for establishing a final position that the syringe plunger is to reach inside the barrel as representative of a reference position, said final position being variable as a function of the size of the barrel, and for providing information related thereto;
a syringe driver slidably mounted on said housing adapted to engage the syringe plunger and impart linear motion thereto for pushing the plunger into the syringe barrel to thereby force the liquid out of the syringe barrel;
a second sensor mounted on said driver for determining a relative position of said plunger with respect to said syringe barrel to relate said relative plunger position to a distance said plunger must travel within the barrel to said final position to expel the liquid therefrom over a pre-selected period of time, said second sensor adapted to provide information related to the determined relative position of said plunger;
a microprocessor regulated servo system, including a motor and drive mechanism, for moving the syringe driver at a controlled speed, further including a variable timing device wherein a period of time, over which the liquid from said syringe barrel is to be expelled, is either selectable by a user of automatically set by the timing device, said servo system being dependent upon said information receiving from the first and second sensors for governing the rate of speed of said driver to expel the liquid from the syringe barrel over the pre-selected period of time; and
a visual display which indicates the current period of time which remains to expel the liquid from the syringe barrel and which continually indicates the originally selected period of time for expelling the liquid from the syringe barrel.

28. An infusion device for the administration of liquid from a syringe having a barrel for holding liquid and a plunger for expelling liquid comprising:
a housing;
a syringe retainer mounted on said housing for receiving a syringe barrel having liquid therein, said retainer including means for receiving syringe barrels of different sizes;
a movable syringe driver mounted on said housing for engaging a syringe plunger and for pushing the plunger into the syringe barrel to thereby force the liquid out of the syringe barrel;
means for measuring the size of the syringe barrel mounted on the housing;
microprocessor control means for storing information representative of a plurality of different size syringe barrels and for comparing the measured syringe barrel with the stored information to categorize the mounted syringe barrel as being of a certain size; and
means for moving said syringe driver against said plunger to expel the liquid from the syringe barrel.

29. The device of claim 28 wherein the microprocessor means for storing is programmable to store information therein representative of standard, conventional size syringe barrels.

30. The device of claim 27 wherein the stored information related to syringe barrels of the following sizes: 3,5,10,20,30 and 60 cubic centimeters.

31. The device of claim 28 wherein the microprocessor means for storing is programmable to store information therein representative of at least three different size syringe barrels.

32. The device of claim 28 wherein the means for storing and the means for comparing are included in microprocessor means.

33. The device of claim 28 wherein the means for measuring the size of the syringe barrel includes stationary means and movable means associated with said syringe retainer for contacting each other at different positions relative to the size of the syringe barrel received in the syringe retainer.

34. The device of claim 33 wherein the stationary means includes a plurality of electrical pads maintained in fixed position on the syringe retainer.

35. The device of claim 34 wherein the movable means includes a plurality of electrical tabs maintained in movable position on the syringe retainer so that the size of the syringe barrel received in the syringe retainer is related to the arrangement of electrical contact between the pads and the tabs.

36. The device of claim 28 wherein the means for moving the syringe driver is movable to expel the liquid from the syringe barrel over a pre-selected period of time at a rate of speed governed by the categorized size of the syringe barrel received in the syringe retainer.

* * * * *